United States Patent [19]
Delmas

[11] Patent Number: 6,004,765
[45] Date of Patent: Dec. 21, 1999

[54] ASSESSMENT OF BONE FRAGILITY AND PREDICTION OF OSTEOPOROTIC FRACTURE RISK USING A QUANTITATIVE DETERMINATION OF CIRCULATING UNDER-CARBOXYLATED OSTEOCALCIN

[76] Inventor: Pierre Delmas, 50 Rue Feuillat, 69003 Lyons, France

[21] Appl. No.: 08/442,138

[22] Filed: May 16, 1995

Related U.S. Application Data

[63] Continuation of application No. 08/017,811, Feb. 16, 1993, abandoned.

[30] Foreign Application Priority Data

Feb. 27, 1992 [EP] European Pat. Off. ............. 92400517

[51] Int. Cl.$^6$ .......................... C07K 16/00; G01N 33/53; G01N 33/543
[52] U.S. Cl. .................... 435/7.9; 530/387.1; 530/388.2; 530/389.1; 530/389.8; 530/391.1; 530/391.3; 435/7.93; 435/7.94; 435/70.21; 435/810; 435/975; 436/58; 436/808; 436/811
[58] Field of Search ..................................... 435/7.9, 7.93, 435/7.94, 70.21, 240.27, 810, 975; 436/518, 808, 811; 530/387.1, 388.2, 389.1, 389.8, 391.1, 391.3

[56] References Cited

U.S. PATENT DOCUMENTS 4,438,208  3/1984  Deftos et al. ........................... 436/542

FOREIGN PATENT DOCUMENTS 4008546  9/1990  Germany .

OTHER PUBLICATIONS

Power, M. J. Osteocalcin: Diagnostic Methods and Clinical Applications. Critical Reviews in Clinical Lab Sciences. vol. 28 (4) (1991):pp. 287–235.

John Kanis et al., "The Diagnosis of Osteoporosis", *Journal of Bone and Mineral Research*, 9:1137–1141 (1994) (no month cited on the reference).

Journal of Biological Chemistry; vol. 255 No. 18; Sep. 25, pp. 8685–8691, 1980; "Isolation and Sequence of the Vitamin K–dependent Protein from Human Bone".

Journal of Bone and Mineral Research, vol. 6, No. 11, 1991 "Impairment of Gamma Carboxylation of Circulating Osteocalcin (Bone Gla Protein) in Elderly Women"; Plantlech et al.

Menon et al., "Impaired Carboxylation of Osteocalcin in Warfarin–Treated Patients", *J. Clin. Endocrin. Metab.*, vol. 64, No. 1, (1987), pp. 59–61.

Hodges et al., "Depressed Levels of Circulating Menaquinones in Patients w/osteoporotic Fractures of The Spine and Femoral Neck," *Bone*, vol. 12, (1991), pp. 387–389.

Szulc et al., "Serum Undercarboxycated Osteocalcin is a Marker of the Risk of Hip Fracture in Elderly Women," *J. Clin. Investg.*, vol. 91, (1993), pp. 1769–1774.

*Primary Examiner*—James C. Housel
*Assistant Examiner*—Pensee T. Do
*Attorney, Agent, or Firm*—Merchant & Gould P.C.

[57] ABSTRACT

A method for the assessment of bone fragility and osteoporosis fracture risk characterized by:
  measuring in vitro the concentration of under-carboxylated osteocalcin in a biological fluid sample such as serum, plasma or urine;
  comparing the concentration of under-carboxylated osteocalcin in the test sample with the concentration in a control sample containing levels of under-carboxylated osteocalcin representative of the upper limit of the normal range, concentrations above this upper limit being indicative of increased risk of bone fracture.

28 Claims, No Drawings

ASSESSMENT OF BONE FRAGILITY AND PREDICTION OF OSTEOPOROTIC FRACTURE RISK USING A QUANTITATIVE DETERMINATION OF CIRCULATING UNDER-CARBOXYLATED OSTEOCALCIN

CROSS-REFERENCE TO RELATED APPLICATIONS

The present application is a file wrapper continuing application of U.S. Ser. No. 08/017,811 filed Feb. 16, 1993, now abandoned. Application Ser. No. 08/017,811 is a national stage application of European Application No. EO 92400517.6 filed Feb. 27, 1992.

The present invention concerns a method for the assessment of bone fragility and osteoporotic fracture risk using a quantitative determination of circulating under-carboxylated osteocalcin (ucOC). The invention further concerns a kit for carrying out the determination, and antibodies suitable for use in the test.

Osteoporosis is a fragility of the bones often found in the ageing population, especially in women, and is characterised by a high incidence of "fragility fractures" i.e. non-traumatic or mildly traumatic fractures. Clinical investigation, and assessment of the risk of osteoporosis is particularly difficult because the anormalities of bone metabolism which characterise the condition are extremely complex and subtle, often occuring very gradually over long periods of time.

Thus, measurement of parameters of bone turnover, i.e. the equilibrium between the formation of new bone by osteoblasts and the resorption of old bone by osteoclasts, often used in the study of other bone diseases involving dramatic metabolic modifications like Paget's disease or renal osteodystrophy, are of limited use in osteoporosis. Indeed, conventional "markers" of bone formation and bone resorption, for example serum osteocalcin and urinary pyridinoline respectively, may be found to be in the normal range in some patients with osteoporosis. Since osteoporosis is often associated with a low bone mass, bone mass measurements using absorptiometry can in some cases be useful. However, this method of assessment of bone fragility is indirect, expensive, and does not provide information about the subsequent rate of bone loss, nor does it provide information about the quality of bone structure.

In an attempt to improve the assessment of the risk of osteoporosis, most systems currently used combine bone mass and bone turnover measurements, the latter parameter being determined by several different markers and being confirmed by invasive techniques such as histomorphometry. To date, no biochemical marker of bone fragility, and hence of bone fracture risk, has been described.

It is an object of the present invention to provide such a biochemical marker.

The present invention is based on the discovery, by the inventors, that levels of circulating under-carboxylated osteocalcin are predictive of the subsequent risk of bone fracture.

Osteocalcin, also called bone gla protein, is a unique non collagenous protein of the extra cellular matrix of bone that is synthesized by the bone forming cells, the osteoblasts. Osteocalcin has 49 amino-acids, including three residues of gamma-carboxyglutamic acid (GLA), an amino acid resulting from the vitamin K-dependent post-translational modification of glutamic acid residues (GLU) within the molecule. The carboxylated GLA residues are at positions 17, 21 and 24. Osteocalcin inhibits hydroxyapatite formation in vitro and is modulated by the calcium regulating hormone 1,25-dihydroxyvitamin D, but its precise physiological functions remain elusive. Osteocalcin has chemotactic properties and may play a role in the initiation of osteoclast recruitment and bone resorption, but this is still speculative.

Because part of the newly synthesized osteocalcin molecules leaks into the circulation, serum levels of osteocalcin have been used as an index of bone formation. Several studies have shown that serum osteocalcin is a sensitive and specific index of the rate of bone formation in various metabolic bone diseases, and renal disorders. Serum osteocalcin is also a useful marker of the effects of specific treatment that will affect bone metabolism and bone mass. The assay of serum osteocalcin relies on the use of polyclonal and/or monoclonal antibodies that quantitate the amount of circulating osteocalcin molecules, regardless of their degree of gamma carboxylation. (Delmas P. D., 1990, Endocrinol. Clin. North Am. 19: 1–18). Recently, Koyama et al (1991, J. Immunol. Meth. 139, 17–23) reported use of monoclonal antibodies specific for fully carboxylated osteocalcin in an osteocalcin assay.

In 1981, Price et al (J. Biol. Chem. 256, n 24, pp 12760–12766, 1981) demonstrated that chronic injections of warfarin, a potent inhibitor of the gamma carboxylation process, result in an under-carboxylation of osteocalcin. The role of γ-carboxyglutamic acid in osteocalcin is to enable the protein to bind strongly to hydroxyapatite, the major constituent of bone. Under-carboxylated osteocalcin is therefore no longer capable of being incorporated into the bone matrix and is released into the circulation. According to the method of Price, measurement of non-carboxylated osteocalcin in the serum is performed by a standard radio immunoassay after incubation of the serum with hydroxyapatite. The carboxylated fraction of the total osteocalcin binds to the hydroxyapatite and the non-carboxylated fraction is measured in the supernatant, using antibodies which have equal affinity for both carboxylated and non-carboxylated osteocalcin.

Using this hydroxyapatite incubation technique, an under-carboxylation of circulating osteocalcin has been shown in patients on anti-coagulant therapy (Pietschmann, P., et al, J. Clin. Endocrin. Metab., 1988, 66, 5, p 1071–1074).

Recently, Plantalech, L., et al (J. Bone Miner. Res., 1991, 6, 11, p 1211–1216) showed that circulating levels of non-carboxylated osteocalcin are markedly increased in elderly women compared to the average levels found in young controls. Furthermore, a significant number of elderly women had non-carboxylated osteocalcin levels which were greater than the upper limit of the normal range. These increased levels are thought to be due to an impairment of the carboxylation of newly synthesised osteocalcin molecules rather than to the decarboxylation of a previously fully carboxylated molecule. Levels of non-carboxylated osteocalcin were compared in women with and without a previous history of bone fracture and no significant difference was found. The non-carboxylated osteocalcin measurements were carried out using the hydroxyapatite binding assay of Price which is indirect, and not very sensitive. This document does not discuss the significance of the elevated under-carboxylated osteocalcin levels and gives no indication that they are related to decreased bone mass and increased bone fragility, characteristic of osteoporosis.

An increase in serum non-carboxylated osteocalcin in elderly women, measured as a percentage of total OC, has also been reported by Knapen et al (Ann. Intern. Med. 111: 1001–1005, 1989). Again the hydroxyapatite binding method was used. Assay conditions are not detailed in the article. No link to bone fragility is made.

The present invention concerns a method for the assessment of bone fragility and bone fracture risk involving the specific determination of circulating under-carboxylated osteocalcin levels. More particularly, the present invention concerns a method for the assessment of bone fragility and bone fracture risk characterised by:

measuring in vitro the concentration of under-carboxylated osteocalcin in a biological fluid sample such as serum, plasma or urine;

comparing the concentration of under-carboxylated osteocalcin in the test sample with the concentration in a control sample containing levels of under-carboxylated osteocalcin representative of the upper limit of the normal range, concentrations above this upper limit being indicative of increased risk of bone fracture.

According to a preferred embodiment of the invention, the measurement of the concentration of under-carboxylated osteocalcin is effected by means of at least one monoclonal antibody or polyclonal antibodies or fragments thereof, said antibodies or fragments being specific for under-carboxylated osteocalcin.

In the context of the present invention, the expression "under-carboxylated osteocalcin" (ucOC) signifies osteocalcin having less than the normal number of GLA residues. Normally, the osteocalcin molecule has 3 GLA residues, therefore "under-carboxylated" signifies molecules having either 0, 1 or 2 GLA residues. For osteocalcin molecules bearing 1 or 2 GLA residues, these residues may be at any of the positions 17, 21 or 24. The GLA group at the 17 position is often missing in under-carboxylated molecules. Under-carboxylated osteocalcin is also referred to as non-carboxylated osteocalcin or ncOC. For purposes of the invention, the expressions will be used interchangeably. The expression ucOC should also be construed to include fragments of under-carboxylated osteocalcin which are specific to the under-carboxylated molecule and which do not occur in the fully carboxylated form of osteocalcin.

According to the method of the invention, the specific measurement of the ucOC levels in the biological sample is preferably carried out using antibodies or fragments thereof which are specific for the under-carboxylated form of the molecule, "specific" meaning that in any given set of reaction conditions the same antibody will react with under-carboxylated osteocalcin with a higher affinity than with fully carboxylated osteocalcin. Normally, in the conditions applied during the test, no cross-reaction with fully carboxylated osteocalcin is observed.

The antibodies suitable for use in the method of the invention may be a polyclonal sera specific for osteocalcin molecules bearing 0, 1 or 2 carboxy groups.

The antibody may also be a monoclonal antibody recognising any one of the epitopes specific for under-carboxylated osteocalcin. A cocktail of such monoclonal antibodies may also be used. It is particularly preferred, according to the present invention, to use an antibody which recognises an epitope occuring in the region of amino acids 17–24 of the under-carboxylated osteocalcin molecule.

Another type of antibody which is particularly advantageous is a conformational antibody recognising the tertiary structure associated with the γ-carboxylation status of osteocalcin. Indeed, DELMAS et al (Biochemistry, 1984, 23, p 4720–4725) have shown major conformational changes of osteocalcin which depend on the degree of γ-carboxylation and on the presence or absence of calcium. An example of this type of conformational antibody is the antibody described in the paper by DELMAS et al, 1984, supra, (Serum R 102) whose binding to osteocalcin is calcium-dependent if osteocalcin is fully carboxylated but not if osteocalcin is not γ-carboxylated.

It is also possible to use, in the method of the invention, fragments of antibodies, provided that the specificity for under-carboxylated osteocalcin is maintained. Such fragments are exemplified by Fab, F(ab')$_2$, Fab' or Fab fragments. Of particular interest are the Fab and F(ab')$^2$ fragments. These fragments are produced by papain digestion and pepsin digestion of the whole antibody, respectively.

The antigens used in the production of the specific antibodies include human, ovine or bovine osteocalcin which has been partially or totally decarboxylated by thermal or chemical methods such as the method described by MERLE et al, 1990, Bone and Mineral, 11, p 207–245. Bovine and ovine osteocalcin are homologous to human osteocalcin between amino acids 20 and 49, and 12 and 49, respectively. It is also possible to use authentic under-carboxylated human, ovine or bovine, osteocalcin occuring in its native form or as the result of warfarin treatment. However, human osteocalcin is very unstable and can be difficult to purify. Isolation of sufficient amounts of under-carboxylated human osteocalcin to enable antibody production is therefore cumbersome. To overcome this problem, it is particularly preferred to use recombinant under-carboxylated osteocalcin such as that expressed in *E. coli*. Indeed the recombinant ucOC is free of GLA residues, and can be produced in large quantities.

Synthetic under-carboxylated osteocalcin can also be used as antigen as well as synthetic peptides corresponding to fragments of the ucOC provided that these fragments bear epitopes specific for under-carboxylated osteocalcin or represent at least a part of the tertiary structure of the under-carboxylated molecule. Particularly preferred fragments are those including the amino acids 17–24. Generally, the fragments will contain at least 8 amino acids, for example 10 to 20. Synthetic osteocalcin or fragments thereof are particularly advantageous in so far as molecules bearing either 0, 1 or 2 GLA residues can be synthesised as desired, which then enables the production of antibodies specifically recognising the different degrees of under-carboxylation. Fragments missing the GLA group at the 17 position are particularly preferred in the raising of antibodies. Fragments of under-carboxylated osteocalcin for use as antigen in raising the antibodies may also be made by cleavage of the whole under-carboxylated osteocalcin molecule, for example by acid cleavage, giving a fragment composed of amino acids 15–48, or tryptic cleavage, giving a fragment 21–42, or V8-protease digestion giving a fragment 8–31.

The polyclonal and monoclonal antibodies of the invention are produced according to conventional techniques, using the above mentioned immunogens. Their specificity for under-carboxylated osteocalcin is ensured by screening of the produced antibodies with both carboxylated and under-carboxylated osteocalcin, and synthetic peptides, in the presence and in the absence of $Ca^{2+}$, and selection of those antibodies which show a much lower cross-reactivity with the carboxylated than with the under-carboxylated form or no cross-reaction at all. Antibodies having specificities for the osteocalcin molecule bearing either 0, 1 or 2 GLA molecules can be selected by contacting the antibodies with molecules having a number of carboxy groups different from that whose specificity is sought.

It is advantageous to verify the sensitivity of the selected antibodies to ensure the accurate detection of concentrations of non-carboxylated osteocalcin typically occuring in serum, for example 0.5 ng/ml.

According to the method of the invention, the under-carboxylated osteocalcin levels may be measured as an absolute value or as a percentage of total circulating osteocalcin. Both paramaters are a marker of bone fracture risk although the absolute value is particularly preferred. In the case of measurement as a percentage of total circulating osteocalcin, the total levels can be determined using antibodies such as those described previously which have equal affinities for the carboxylated and the non-carboxylated molecules. Alternatively, the total levels can be determined using an antibody such as that described by DELMAS et al (Biochemistry, 1984, 23, 4720–4725). In the absence of divalent metal ions, such antibodies are specific for the under-carboxylated form. Addition of metal ions, such as calcium or magnesium, render the antibody capable of recognising also the carboxylated form. Using this last method, both under-carboxylated and total osteocalcin can be measured quickly and conveniently since the same antibody comes into play for each measurement.

According to the method of the invention, the biological fluid sample may be serum, plasma, urine or blood. Serum is particularly preferred. The biological fluid samples may vary in volume from about 10 to about 250 μl, for example 50 to 100 μl.

The patients from whom the samples are taken must not be on anti-coagulant therapy, using a vitamin K antagonist, since such medicaments cause an increase in circulating non-carboxylated osteocalcin levels and would therefore falsify the results. Most commonly, the patients will be post-menopausal women, but the assessment of the risk in elderly men is also valuable.

In carrying out the method of the invention, the specific antibodies are contacted with the sample of biological fluid, the reaction conditions being such as to allow the quantitative detection of the under-carboxylated osteocalcin. Once the levels in the sample have been determined, they are compared with a control sample containing under-carboxylated osteocalcin at levels representative of the upper limit of the normal range in young people. The upper limit of the normal range is defined as the mean value of non-carboxylated osteocalcin levels+two standard deviations (mean+2SD). This value is determined in a group of premenopausal healthy women aged for example 31±7 years and using the same experimental conditions and reagents as those to be used in the test. The group of premenopausal women should normally consist of at least 20 women. They should be healthy with no history of metabolic bone disease and should not be taking any drug known to affect bone metabolism, nor anticoagulants of the vitamin-K antagonist type. The precise value of the upper limit of the normal level varies according to the experimental conditions and reagents used, for example the antibody. To date, using the hydroxyapatite-binding method, the upper limit of the normal range of under-carboxylated osteocalcin has been calculated as the mean+2 standard deviations and is approximately 1.65 ng/ml (16.7% of total). It is emphasised that this limit represents the upper limit of the normal range using this technique which provides an indirect and relative value.

The present inventors have found that when testing a population of elderly women for assessment of osteoporosis, most subjects show ncOC levels higher than the average value found in young controls (for example, greater than 0.65 ng/ml). However, some subjects will show levels greater than the upper limit (for example, greater than 1.65 ng/ml). These latter subjects are those with greatly increased risk of fracture. Risk increases as levels increase above this threshold value.

The detection of the antigen/antibody reaction is made possible by use of conventional detection techniques. Particularly preferred is the use of competition radio immunoassay in which the detection means is radio labelled non-carboxylated osteocalcin, for example using $^{125}$I. According to this embodiment, specific antibody is bound to a solid phase and a mixture of test (unlabelled) and labelled uncarboxylated osteocalcin is applied. The labelled and unlabelled antigens compete with each other for the antibodies' binding sites. The greater the amount of test antigen that is present, the less labelled antigen will bind to the antibody. Calibration curves using known quantities of unlabelled antigens are established.

Another method of detection is a competitive enzyme immunoassay using enzyme labelled non-carboxylated osteocalcin. Suitable enzyme labels have been described by TANAKA et al (Journal of Immunological Methods, 1984, p 1924–1986).

A further possibility is a sandwich enzyme immunoassay in which two monoclonal antibodies are selected which bind to two different sites on the under-carboxylated osteocalcin molecule. One of these antibodies is a "capture" antibody, and is preferably immobilised on a solid support and the other antibody is a "detector" antibody. The detector antibody is enzyme labelled or can be radiolabelled, for example with $^{125}$I.

The sensitivity of the assay according to the invention is, preferably at least, 0.2 ng/ml.

Once the increased risk of bone fragility, the hallmark of osteoporosis, has been diagnosed, a suitable therapeutic intervention which can reduce the rate of bone loss and reduce the risk of fracture can be applied. The present inventors have demonstrated that administration of Vitamin D to subjects having high non-carboxylated osteocalcin levels has the effect of partially correcting these levels. The inventors have also shown that non-carboxylated osteocalcin levels are a marker for Vitamin D deficiency in the elderly. Indeed, Vitamin D deficiency is a well recognised risk factor for osteoporosis. The test of the present invention therefore allows simultaneous assessment of osteoporotic fracture risk and Vitamin D status.

The invention further relates to a kit for the assessment of bone fragility and bone fracture risk by quantitative determination of circulating under-carboxylated osteocalcin, said kit comprising:

means for measuring the concentration of under-carboxylated osteocalcin in a biological fluid sample such as serum, plasma or urine;

any necessary detection means.

Preferably, the kit contains as means for measuring the concentration of ucOC at least one monoclonal antibody or polyclonal antibodies or fragments thereof, said antibodies or fragments being specific for under-carboxylated osteocalcin, together with means for detecting the antigen-antibody reaction and optionally, divalent metal ions such as $Ca^{2+}$.

The antibodies and the detection means included in the kit of the invention are those described above. The antibodies are preferably immobilised on a solid support such as membranes, vessel walls or microspheres.

The kit of the invention may further contain divalent metal ions such as $Ca^{2+}$, for example in the form of calcium chloride. The inclusion of calcium is advantageous when the antibodies are of the conformational type.

The kit may also further comprise one or two control samples containing known levels of under-carboxylated osteocalcin enabling a comparison of the sample to be measured with the threshold defined by the assay. The threshold value (upper limit of the normal range) is defined as indicated above.

The invention also relates to the monoclonal and polyclonal antibodies described above which are suitable for use in carrying out the quantitative determination of the invention. These antibodies preferably show a poor cross reaction with carboxylated osteocalcin, whatever the reaction conditions, such as presence of metal ions. Their sensitivity is such as to enable detection of non-carboxylated osteocalcin at levels of around 0.5 ng/ml, and preferably 0.2 ng/ml.

EXAMPLES

I—Measurement of Carboxylated (carbOC) and Non-Carboxylated (ncOC) Osteocalcin and Other Parameters of Bone Metabolism in Biological Samples, and Correlation with Subsequent Risk of Hip Fracture:

Total OC, ncOC, calcium, phosphate, parathormone (PTH), 25-hydroxy vitamin D (25 OHD), alkaline phosphatase and creatinine were measured in the sera of 195 elderly institutionalised women (70–101 years).

Women with serious medical conditions were excluded from the study as well as women receiving medicines affecting bone metabolism, vitamin D and/or calcium (during more than one year), sodium fluoride (during more than 3 months) and warfarin homologues (at the moment of the recruitment).

The osteocalcin level was measured with the previously described radioimmunoassay/hydroxyapatite method (Merle, B. et al, 1990, Bone Miner. 11: 237–245) using rabbit polyclonal antiserum (AS 140) which has the same affinity for ncOC and carbOC. The hydroxyapatite-bound OC was precipitated with a mixture of sheep anti-rabbit IgG antiserum and polyethylene glycol (PR CIS BIO Industrie, France) and centrifuged. The precipitate was rinsed with the assay buffer and recentrifuged. The sensitivity of this assay is 0.2 ng/ml. The method of measurement of the ncOC based on the different affinities of carbOC and ncOC for hydroxyapatite, is described in the article of Merle, B. et al (supra). Briefly, 250 $\mu$l samples were incubated with 5 and 10 mg of hydroxyapatite (Calcium Phosphate Tribasic type IV, Sigma Chemicals) in an Eppendorf tube and mixed end over end for one hour at +4° C. and than centrifuged. These amounts of hydroxyapatite provide the best discrimination between the binding capacities of carbOC and ncOC present in 250 $\mu$l of serum. The ncOC concentration was calculated as the mean of concentrations measured in both supernatants (with 5 and 10 mg of hydroxyapatite). The ncOC level was also expressed as the percent of total OC concentration (ncOC%). CarbOC concentration was calculated as the difference between total OC and ncOC.

The upper limits of the normal range for OC and its fractions were calculated as the mean±2SD (Standard Deviation) in 21 healthy, premenopausal women, aged 21–44 years. For this method of determination these limits are: 13.9 ng/ml for total OC, 12.5 ng/ml for carbOC, and 1.65 ng/ml (16.7% of total) for ncOC.

The serum concentrations of calcium, inorganic phosphorus, total protein and creatinine were measured using conventional techniques. The intact parathormone (PTH) concentration was measured using the Magic Lite Intact PTH Immunoassay (CIBA CORNING). The 25OHD level was determined using a kit (Buhlmann Laboratories AG, Switzerland). The alkaline phosphatase activity was measured using Automated Analysis Boehringer Mannheim.

Serum ncOC was found to be increased in elderly women (1.18±0.12 ng/ml) compared to young controls (0.65±0.11 ng/ml, p<0.01). In 45 women (23.1%) serum ncOC was above the upper limit of the normal range for young women (ie >1.65 ng/ml). NcOC was negatively correlated with 25OHD (r=−0.32, p<0.001) even after excluding the effect of age, PTH and creatinine by partial correlation (r=−0.24, p<0.002). This last observation is particularly interesting, signifying that the higher ncOC levels, the lower the Vitamin D levels. NcOC levels are therefore a marker for Vitamin D deficiency in the elderly, a well recognised risk factor for osteoporosis.

The women were then prospectively followed for 18 months and medical status, treatment, and occurence of fractures were recorded every 6 months. They were randomised to either Ca (1.2 g/d) and Vit D (800 U/d) or to a double placebo as a part of a prospective trial on the effect of Ca and Vit D on the incidence of hip fracture. During the 18 months follow-up, 15 women sustained a hip fracture and their baseline biochemical measurements were compared to those of the 180 who did not fracture.

The results are summarised in Table I:

|  | Fracture + | Fracture − |  |
|---|---|---|---|
| Age (years) | 86.33 ± 5.64 | 83.28 ± 5.07 | p = NS |
| OC total (ng/ml) | 7.82 ± 4.01 | 6.36 ± 3.44 | p = NS |
| OC carbox (ng/ml) | 6.35 ± 3.16 | 5.42 ± 2.75 | p = NS |
| OC noncarb (ng/ml) | 1.62 ± 1.16 | 0.94 ± 0.93 | p < 0.01 |
| OC noncarb % | 18.61 ± 11.06 | 12.64 ± 8.11 | p < 0.01 |
| 25 (OH) D3 | 14.07 ± 8.26 | 16.61 ± 12.42 | p = NS |
| PTH | 61.77 ± 26.81 | 49.60 ± 29.64 | p = NS |
| Alk. phosph. | 4.42 ± 1.33 | 4.33 ± 2.13 | p = NS |

NS = not significant

Table I: Comparison of ncOC, carboc, Total OC and Conventional Calcium Metabolism Parameters in Women Sustaining Hip Fracture with those in the Non-Fracture Group These results show that ncOC was higher in women who subsequently sustained hip fracture than in the non fracture group, contrasting with no significant differences for Alk. Ph., PTH, 25OHD, total and carboxylated OC and other parameters such as serum calcium, phosphate and creatinine. The risk of hip fracture, evaluated using Odds Ratio (O.R., calculated according to the Mantel-Haenszel method) adjusted for treatment for the treatment group (Ca+Vit. D/placebo), for diseases and for drugs known to affect the hip fracture risk, was increased in women with elevated ncOC concentration (>1.65 ng/ml): O.R. 7.1, 99.9% CI 1.1–46.3, p<0.001, and in those with elevated ncOC % (>16.7%) (O.R.=3.9, 95% CI 1.4–11.3, p<0.05). In other words, women having levels of ncOC above the upper limit of the normal range, expressed either as an absolute value or as a percentage of total OC, were seven times more prone to subsequent hip fracture than those having levels less than the upper normal limit.

The women who sustained fractures were not older. When baseline biochemical measurements were compared in both groups only ncOC (p<0.01) and ncOC % (p<0.01) were elevated in the patients who later sustained hip fracture. Other parameters did not differ significantly.

In conclusion, ncOC and ncOC % are the only parameters which have predictive value in assessing bone fracture risk. Conventional calcium metabolism parameters have no predictive value. Serum ncOC therefore appears to reflect changes in bone matrix associated with increased fragility.

As far as the effect of Ca and Vitamin D on the incidence of hip fracture is concerned, it was observed that during one year of Vit D/Ca treatment, ucOC decreased (p<0.05), especially in those with the initially increased values (from 2.5±0.41 to 1.41±0.29 ng/ml, p<0.005), contrasting with an increase of ncOC in the placebo group (p<0.05).

Since vitamin K plays a major role in the gamma carboxylation of the GLA-containing proteins, serum levels of Vit K1 and of the major circulating moeities of Vit K2, menaquinone-7 (MK-7) and menaquinone-8 (MK-8) were measured in 51 patients with hip-fracture. Results showed that serum K1, MK-7 and MK-8 were decreased in hip fracture patients when compared to age and sex-matched controls (for example, Vit K1: 336±302 vs 585±490 pg/ml, p<0.01). These data indicate the existence of Vitamin K deficiency in elderly subjects with hip fracture. The fact that undercarboxylation of circulating OC is related, to some degree, to Vitamin K deficiency is also supported by the fact that low doses of Vit K1 (1 mg/day) reduce significantly ucOC levels (see Plantalech, L. et al, In Osteoporosis 1990, ED.: C. Christiansen and K. Overgaard p 345–347 and Knapen MHJ et al. Ann. Int. Med. 1989, 111: 1001). The test of the invention therefore also allows assessment of vit. K status.

II—Assessment of Bone Fragility Using Specific Antibodies to Measure ncOC Levels:

Antiserum against fully carboxylated OC was raised in rabbits as previously described (DELMAS et al, 1983, J. Clin. Invest, 71, 1316–1321). The antiserum chosen for this assay was chosen on the basis of its $Ca^{2+}$ dependence of binding. A similar serum has been described in detail in Delmas et al., 1984 Biochemistry, 23, 4720–4725.

In the presence of $Ca^{2+}$ or other divalent metal ions such as $Mg^{2+}$, the antiserum binds carboxylated and thermally decarboxylated OC with the same affinity. Upon removal of $Ca^{2+}$ with ethylenediaminetetraacetic acid, antibody binding to carboxylated OC is eliminated, while antibody binding to decarboxylated is maintained.

Thus the epitope not expressed by fully carboxylated OC in the absence of $Ca^{2+}$ was restored either by addition of $Ca^{2+}$ or by decarboxylation. In addition, circular dichroic studies indicated that these $Ca^{2+}$- and GLA- dependent antibody binding changes were associated with changes in the tertiary structure of the molecule (apparent α-helix). Taken together, these data suggest the existence of conformational epitopes of OC that will depend on the carboxylation status of the molecule.

This type of antibodies is suitable for use in the assay of invention.

I claim:

1. A method for the assessment of bone fragility and osteoporosis fracture risk comprising:
    (a) measuring in vitro by immunoassay the concentration of under-carboxylated osteocalcin in a biological fluid sample using at least one monoclonal antibody or fragments thereof wherein said antibodies or fragments differentially specifically bind under-carboxylated osteocalcin with a higher affinity than fully carboxylated osteocalcin such that, in the absence of $Ca^{2+}$ or $Mg^{2+}$, no-cross reaction with fully carboxylated OC is observed; and
    (b) comparing the concentration of under-carboxylated osteocalcin in the test sample with the concentration in a control sample containing levels of under-carboxylated osteocalcin representative of the upper limit of the normal range, concentrations above this upper limit being indicative of increased risk of bone fracture.

2. The method according to claim 1 wherein the concentration of under-carboxylated osteocalcin is measured as an absolute value.

3. The method according to claim 1 wherein said antibody specifically binds to an epitope occurring in the region of amino acids 17–24 of the under-carboxylated osteocalcin molecule.

4. The method according to claim 1 wherein the antibody fragments are Fab fragments.

5. The method according to claim 1 wherein the specific antibodies are raised to under-carboxylated osteocalcin which is selected from the group consisting of native of warfin-induced human under-carboxylated osteocalcin; native human, ovine or bovine osteocalcin which has been decarboxylated osteocalcin; synthetic under-carboxylated osteocalcin and fragments of any of the foregoing wherein said fragments bear epitopes that do not occur in the fully-carboxylated form of osteocalcin.

6. The method according to claim 1 wherein said monoclonal antibody recognizes an epitope that does not occur in the fully-carboxylated form of osteocalcin, or a plurality of such antibodies.

7. The method according to claim 1 wherein said antibody specifically binds to an epitope occurring in the region of acids 17–24 of the under-carboxylated osteocalcin.

8. A method according to claim 1 wherein the antibody detects levels of under-carboxylated osteocalcin of about 0.2 ng/ml.

9. A kit for the assessment of bone fragility and bone fracture risk by quantitative determination of circulating under-carboxylated osteocalcin, said kit comprising:
    (a) means for specifically measuring the concentration of under-carboxylated osteocalcin in a biological fluid sample said means comprising at least one monoclonal antibody or fragments thereof, wherein said antibodies or fragments differentially specifically bind under-carboxylated osteocalcin with a higher affinity than fully carboxylated osteocalcin such that in the absence of $Ca^{2+}$ or $Mg^{2+}$, no-cross-reaction with fully carboxylated OC is observed; and
    (b) means for detecting an antigen-antibody reaction.

10. The kit according to claim 9 wherein said antibody is a monoclonal antibody specifically binding to an epitope that does not occur in the fully-carboxylated form of osteocalcin, or a plurality of such monoclonal antibodies.

11. The kit according to claim 9 wherein said antibody recognizes an epitope occurring in the region of amino acids 17–24 of the under-carboxylated osteocalcin molecule.

12. The kit according to claim 9 wherein the antibody fragments are Fab fragments.

13. The kit according to claim 9 wherein the specific antibodies are raised to under-carboxylated osteocalcin which is selected from the group consisting of native human or bovine under-carboxylated osteocalcin; native human or bovine osteocalcin which has been decarboxylated by thermal or chemical methods; recombinant under-carboxylated osteocalcin; synthetic under-carboxylated osteocalcin; and fragments of any of the foregoing, wherein said fragments bear epitopes that do not occur in the fully-carboxylated form of osteocalcin.

14. The kit according to claim 9 in which the detection means is chosen from the group consisting of radio-labelled non-carboxylated osteocalcin, enzyme-labelled non-carboxylated osteocalcin, and enzyme-labelled antibodies recognizing an epitope of non-carboxylated osteocalcin different from that recognized by the antibody or fragment that specifically binds under-carboxylated osteocalcin.

15. The kit according to claim 9 wherein the antibodies are immobilized on a solid support.

16. A monoclonal antibody or fragments thereof, which bind to under-carboxylated osteocalcin with a higher affinity than fully-carboxylated osteocalcin such that, in the absence of $Ca^{2+}$ or $Mg^{2+}$, no-cross-reaction with fully carboxylated osteocalcin is observed.

17. The antibody or fragments according to claim 16, wherein the antibody or fragments recognizes the 21 and/or 24 Glu position of under-carboxylated osteocalcin.

18. The antibody or fragment according to claim 16 wherein the antibody or fragment recognizes an epitope occurring in the region of amino acids 17–24 of the under-carboxylated osteocalcin.

19. A method for the assessment of bone fragility and osteoporosis fracture risk comprising:
    (a) contacting at least one monoclonal antibody with a biological fluid to quantitatively detect the concentration of under-carboxylated osteocalcin, wherein said monoclonal antibody specifically binds to an epitope occurring in the region of amino acids 17–24 of the under-carboxylated osteocalcin molecule and recognizes the 21 and/or 24 Glu position of under-carboxylated osteocalcin and wherein said monoclonal antibody differentially specifically binds under-carboxylated osteocalcin such that, in the presence or absence of $Ca^{2+}$ or $Mg^{2+}$, no-cross-reaction with fully carboxylated OC is observed; and
    (b) comparing the concentration of under-carboxylated osteocalcin in the test sample with the concentration in a control sample containing levels of under-carboxylated osteocalcin representative of the upper limit of the normal range, concentrations above this upper limit being indicative of increased risk of bone fracture.

20. The method according to claim 19, wherein said monoclonal antibody recognizes an epitope that does not occur in the fully-carboxylated form of osteocalcin, or a plurality of such monoclonal antibodies.

21. The method according to claim 19, wherein the concentration of under-carboxylated osteocalcin is measured as an absolute value.

22. The method according to claim 19, wherein the antibody detects levels of under-carboxylated osteocalcin of about 0.2 ng/ml.

23. A method for the assessment of bone fragility and osteoporosis fracture risk comprising:
    (a) contacting polyclonal antibodies with a biological fluid to quantitatively detect the concentration of under-carboxylated osteocalcin, wherein said polyclonal antibodies specifically binds to an epitope occurring in the region of amino acids 17–24 of the under-carboxylated osteocalcin molecule and wherein said polyclonal antibodies differentially specifically binds under-carboxylated osteocalcin such that, in the absence of $Ca^{2+}$ or $Mg^{2+}$, no-cross-reaction with fully carboxylated OC is observed; and
    (b) comparing the concentration of under-carboxylated osteocalcin in the test sample with the concentration in a control sample containing levels of under-carboxylated osteocalcin representative of the upper limit of the normal range concentrations above this upper limit being indicative of increased risk of bone fracture.

24. The method according to claim 23, wherein said polyclonal antibodies recognizes an epitope that does not occur in the fully-carboxylated form of osteocalcin.

25. The method according to claim 23, wherein the concentration of under-carboxylated osteocalcin is measured as an absolute value.

26. The method according to claim 23, wherein the antibody detects levels of under-carboxylated osteocalcin of about 0.2 ng/ml.

27. The method according to claim 23, wherein said polyclonal antibodies specifically bind to osteocalcin molecules bearing 0 carboxy groups.

28. A monoclonal antibody or fragments thereof, which bind to under-carboxylated osteocalcin with a higher affinity than fully-carboxylated osteocalcin such that, in the presence or absence of $Ca^{2+}$ or $Mg^{2+}$, no-cross-reaction with fully carboxylated osteocalcin is observed wherein said monoclonal antibody specifically binds to an epitope occurring in the region of amino acids 17–24 of the under-carboxylated osteocalcin molecule and recognizes the 21 and/or 24 Glu position of under-carboxylated osteocalcin.

* * * * *